United States Patent [19]

Karra

[11] Patent Number: 4,973,786

[45] Date of Patent: Nov. 27, 1990

[54] PROCESS FOR THE PYROLYTIC OXIDATION OF METHANE TO HIGHER MOLECULAR WEIGHT HYDROCARBONS AND SYNTHESIS GAS

[76] Inventor: Sankaram B. Karra, 321 E. Live Oak, #23, San Gabriel, Calif. 91776

[21] Appl. No.: 110,248

[22] Filed: Oct. 19, 1987

[51] Int. Cl.$^5$ ................................................ C07C 2/00
[52] U.S. Cl. ..................................... 585/500; 585/654; 585/656; 585/700; 585/943
[58] Field of Search ............... 585/700, 506, 415, 417, 585/654, 656, 658, 943, 659, 560

[56] References Cited

U.S. PATENT DOCUMENTS

| | | | |
|---|---|---|---|
| 2,320,274 | 5/1943 | Gorin | 260/673 |
| 2,488,083 | 6/1946 | Gorin et al. | 260/677 |
| 4,199,533 | 4/1980 | Benson | 260/676 R |
| 4,544,784 | 10/1985 | Sofranko | 585/500 |
| 4,620,057 | 10/1986 | Kimble | 585/500 |
| 4,654,460 | 3/1987 | Kimble | 585/500 |
| 4,658,077 | 4/1987 | Kolts | 585/500 |
| 4,714,796 | 12/1987 | Senkan | 585/328 |

OTHER PUBLICATIONS

Wohlfahrt et al., "Preparation of Ethylene-Ethane Mixtures," Chemical Abstracts, vol. 105, 153683m (1986).
Weissman et al., "Pyrolysis of Methyl Chloride, a Pathway in the Chlorine-Catalyzed Polymerization of Methane", International Journal of Chemical Kinetics, vol. 16, pp. 307-333 (1984).
Albright et al., "Pyrolysis: Theory and Industrial Practice", Chapter 1, (Academic Press 1983).
Jones et al., "Fuels for the Future: Remote Gas Conversion" Energy & Fuels, vol. 1, No. 1, pp. 12-16 (1987).

*Primary Examiner*—Olik Chaudhuri
*Assistant Examiner*—James M. Hunter, Jr.

[57] ABSTRACT

A process is disclosed for catalytically converting methane to synthesis gas and one or more saturated or unsaturated higher molecular weight hydrocarbons, such as ethane, ethylene, and acetylene. The process employs a homogeneous gas phase hydrogen halide catalyst other than hydrogen fluoride to faciltiate the pyrolytic oxidation of methane. Alternatively the homogeneous gas phase catalyst may consist of a mixture of gaseous hydrogen halide and gaseous halogen, or a halogen gas.

8 Claims, No Drawings

PROCESS FOR THE PYROLYTIC OXIDATION OF METHANE TO HIGHER MOLECULAR WEIGHT HYDROCARBONS AND SYNTHESIS GAS

FIELD OF THE INVENTION

This invention relates to the field of methane conversion and, in particular, the homogeneous catalytic conversion of methane to synthesis gas and higher molecular weight saturated and unsaturated hydrocarbons.

BACKGROUND OF THE INVENTION

Methane is abundantly available in nature in the form of natural gas, which typically contains about 75% methane by weight. Methane is also produced by other means, such as anaerobic digestion. Although methane is used primarily as a fuel, it is also a valuable starting material in the production of a number of important higher molecular weight saturated and unsaturated hydrocarbons, such as ethane, ethylene and acetylene. These compounds, in turn, are useful starting materials in the production of other commercially important petrochemicals.

Processes are known for converting methane to ethane, ethylene, acetylene, and hydrogen using a technique known as "pyrolysis." Such processes use heat to convert methane into higher molecular weight hydrocarbons without the presence of substantial amounts of oxygen gas or so-called free oxygen. A general discussion of the high temperature pyrolysis of methane can be found, for example, in chapter 1 of *Pyrolysis: Theory and Industrial Practice* (Academic Press, 1983), edited by L. Albright, B. Crynes, and W. Corcoran.

Methane can be converted into higher molecular weight hydrocarbons by a number of other processes which also involve the use of pyrolysis. For example, Gorin U.S. Pat. No. 2,488,083 describes a process for converting methane into normally liquid hydrocarbons by first converting methane into methyl halide, and then pyrolytically condensing the methyl halide into the desired end products. In this process, lower pyrolysis temperatures are made possible by the use of metal-based alumina-silica catalysts.

Sofranko, et al. U.S. Pat. No. 4,544,784 also describes a process for converting methane to higher hydrocarbons by pyrolysis. This process involves the use of heterogeneous reducible metal oxide catalysts with a halogen promoter.

Benson U.S. Pat. No. 4,199,533 describes a method for producing higher molecular weight hydrocarbons by igniting a mixture of methane and recyclable chlorine catalyst in a reaction chamber substantially devoid of free oxygen.

Methane can also be converted into benzene and other aromatic hydrocarbons by first converting it into methyl halide and then pyrolizing the resulting methyl halide. Such a process is described, for example, in Gorin U.S. Pat. No. 2,320,274.

A significant disadvantage to the use of the above processes for methane conversion is that in addition to producing the desired end products, these processes also produce substantial amounts of high surface area solid carbon or soot. Weissman and Benson have experimentally analyzed and verified the phenomenon of carbon soot formation in "Pyrolysis of Methyl Chloride, a Pathway in the Chlorine-Catalyzed Polymerization of Methane," International Journal of Chemical Kinetics, vol. 16, pp. 307-333 (1984). This solid carbon soot by-product, although potentially valuable, is difficult and costly to handle and dispose of. In addition, in substantial quantities, it is responsible for "poisoning," or destroying the effectiveness of, metal-based catalysts which may be used in the methane conversion process. Because of carbon soot formation, the overall cost of the above methods of methane conversion is increased.

Processes are also known for converting methane into so-called "synthesis gas," a mixture of carbon monoxide (CO) and hydrogen ($H_2$). Synthesis gas is an important industrial feedstock, since it can be catalytically converted into methanol and several other useful chemicals in accordance with known processes. Current methods of producing synthesis gas typically involve the reformation of methane with steam at a high temperature (1000° K) in the presence of a metal-based catalyst. One drawback of these processes is the exceedingly high temperatures required. Such high temperatures require a significant expenditure of energy and result in a corresponding increase in the cost of these processes.

None of the methane conversion processes described above are capable of simultaneously producing both higher molecular weight hydrocarbons and synthesis gas in an economically feasible and efficient manner. An efficient process for simultaneously producing higher molecular weight hydrocarbons and synthesis gas would be of great value to the petrochemical industry, since methane could be converted at the well site into feedstock for methanol and other important petrochemicals. The advantages of converting methane into such products at the well site are significant, because the resulting products are substantially less expensive and less dangerous to transport than methane gas.

SUMMARY OF THE INVENTION

The present invention provides a process for simultaneously preparing synthesis gas (carbon monoxide and hydrogen) and one or more saturated or unsaturated higher molecular weight hydrocarbons, such as ethane, ethylene, and acetylene. The invention employs a gaseous hydrogen halide catalyst (other than hydrogen fluoride) to facilitate the pyrolytic oxidation of methane, i.e.. the reaction of methane with free oxygen under conditions of elevated temperature. Alternatively, the catalyst may consist of a mixture of gaseous hydrogen halide (other than fluoride) and gaseous halogen (other than fluorine) or a halogen (other than fluorine) alone.

More specifically, one embodiment of the invention provides a process for preparing synthesis gas (carbon monoxide and hydrogen) and one or more saturated or unsaturated higher molecular weight hydrocarbons. The process comprises reacting methane and free oxygen in the presence of a gaseous hydrogen halide catalyst (other than hydrogen fluoride) under conditions that permit the pyrolytic oxidation of the methane. In a preferred form of this embodiment, the hydrogen halide catalyst used is hydrogen bromide. In another preferred form of this embodiment, the reactants are present in the following molar ratios: methane to oxygen, between about 10:1 and about 1:1, and methane to hydrogen halide, between about 20:1 and about 1:1.

Another embodiment of the invention comprises reacting methane and free oxygen in the presence of a catalyst comprised of a mixture of gaseous hydrogen halide other than hydrogen fluoride and gaseous halogen other than fluorine under conditions that permit the pyrolytic oxidation of the methane. A preferred form of this embodiment uses a mixture of hydrogen bromide and bromine as the gaseous catalyst. In another preferred form of this embodiment, the reactants are present in the following molar ratios: methane to oxygen, between about 10:1 and about 1:1, methane to hydrogen halide, between about 20:1 and about 1:1, and methane to halogen, between about 10:1 and about 1:1.

Another embodiment of the invention provides a process for converting methane into synthesis gas and one or more compounds selected from the group consisting of ethane, ethylene, and acetylene. The process comprises reacting methane, free oxygen, and a catalyst which comprises a mixture of a gaseous hydrogen halide (other than hydrogen fluoride) and a gaseous halogen (other than fluorine) at a temperature above about 500° C. and below about 1000° C. in which the reactants are present in the following molar ratios: methane to oxygen, between about 10:1 and about 1:1, methane to hydrogen halide between about 20:1 and about 1:1, and methane to halogen between about 10:1 and about 1:1.

In another embodiment of the invention, halogen gas other than fluorine is used as gaseous catalyst. The preferred halogen catalyst is bromine. In a preferred form of this embodiment, the reactants are present in the following molar ratios: methane to oxygen, between about 10:1 and about 1:1, and methane to halogen, between about 10:1 and about 1:1.

The process is a one-step conversion process using a gaseous hydrogen halide, a hydrogen halide/halogen gas mixture, or a halogen as recyclable active catalyst and free oxygen as partial oxidative reactant. The process can be operated so as to produce a desired mix of higher molecular weight hydrocarbon end products and synthesis gas. It is simple, economical, and can be readily used at the well site. In addition, the process operates without substantial formation of undesirable by-products, such as solid carbon or soot. Finally, the process operates without production of a destructive flame, in which carbon dioxide ($CO_2$) is produced.

The synthesis gas produced by the process can be used to manufacture a variety of chemicals at the well site, such as methanol, by processes well known in the art. In addition, at normal atmospheric pressure, the process can be operated at lower pyrolytic temperatures: between about 500° C. and about 1000° C. Therefore, at a given pressure, use of the process results in a substantial cost savings over existing processes.

DETAILED DESCRIPTION OF AN EMBODIMENT OF THE INVENTION

In the process of the present invention, the methane, free oxygen, and gaseous hydrogen halide are combined in a reactor in the desired molar ratios. As primary reactant, one can use methane alone or natural gas. In the latter case, the high molecular weight components of the natural gas can be regarded as excess hydrocarbons. Air can be used as the source of oxygen. It is preferred that the reactants be present in the following molar ratio ranges: methane to oxygen, between about 10:1 and about 1:1, and methane to hydrogen halide, between about 20:1 and about 1:1.

The gaseous hydrogen halide used as homogeneous catalyst in the process can be represented by the general formula HX, where X is a halide other than fluoride. The preferred hydrogen halide catalyst is hydrogen bromide. Pyrolytic oxidation takes place under the same conditions used for the pyrolysis of methane or methyl chloride without the presence of substantial amounts of free oxygen. These conditions are described in greater detail in the treatise *Pyrolysis: Theory and Industrial Practice*, which is cited above and incorporated herein by reference. The temperature of pyrolysis is preferably maintained at above 500° C. and, more particularly, between about 500° C. and about 1000° C.

The reaction is preferably maintained at atmospheric pressure by withdrawing products at an appropriate rate. However, the reaction can also be conducted at other pressures. The time for the reaction depends on the operating conditions, the desired degree of conversion, and desired product ratios. Typically, however, the time needed is on the order of several seconds.

In another embodiment of the invention, a mixture of gaseous hydrogen halide and gaseous halogen is employed as homogeneous catalyst. The reaction takes place under the same conditions set forth above. It is preferred that the reactants be present in the following molar ratios: methane to oxygen, between about 10:1 and about 1:1, methane to hydrogen halide, between about 20:1 and about 1:1, and methane to halogen, between about 10:1 and about 1:1. The hydrogen halide component of the catalyst can be represented by the general formula HX, where X is a halide other than fluoride. The halogen component of the catalyst can be represented by the general formula $X_2$, where $X_2$ is a halogen molecule other than fluorine. The preferred catalyst is a mixture of hydrogen bromide and bromine; however, other combinations of hydrogen halide and halogen can be used. Although iodine, or $I_2$, is a solid at room temperature, it is a gas at the temperatures employed during oxidative pyrolysis. Accordingly, it will be understood that $I_2$ may be introduced into the reaction chamber as a gas.

In an alternative embodiment of the invention, halogen gas other than fluorine is used as gaseous catalyst. The preferred halogen catalyst is bromine. In this embodiment, the reactants are preferably present in the following molar rations: methane to oxygen, between about 10:1 and about 1:1, and methane to halogen, between about 10:1 and about 1:1.

The overall reactions believed to be taking place within the reaction chamber, which are more fully described below, are all equilibria reactions. Accordingly, the composition of the resultant products can be controlled by varying the ratio of reactants, the temperature, and/or the pressure within the reactor, as is well known in the art. Along with the production of carbon monoxide, hydrogen, ethane, ethylene, and acetylene, small amounts of higher homologues and halogenated hydrocarbons are produced.

The products of the reaction are separated into various desirable components or mixtures of components using well known separation techniques. One such method is fractionation, which is described in Gorin U.S. Pat. No. 2,488,083 and Benson U.S. Pat. No. 4,199,533. After separation of the various products, the excess unreacted methane may be recycled to the reaction chamber.

It is believed that a number of equilibria reactions take place in the reactor. One such reaction produces carbon monoxide and hydrogen at the stoichiometric ratio of methane to oxygen. It is believed that the reaction proceeds according to the following thermodynamically favorable equation:

$$CH_4 + O_2 + 2HX \rightarrow CO + 2H_2 + H_2O + X_2, \qquad (1)$$

where X represents a halide other than fluoride and $X_2$ represents a halogen molecule other than fluorine.

Another reaction produces the higher molecular weight hydrocarbons, such as ethane, ethylene and acetylene, at the stoichiometric mole ratio of methane to oxygen, or with methane in excess. It is believed that the reaction proceeds according to the following thermodynamically favorable equations:

$$2CH_4 + O_2 + 2HX \rightarrow C_2H_6 + 2H_2O + X_2 \qquad (2)$$

$$2CH_4 + O_2 + 2HX \rightarrow C_2H_4 + H_2 + 2H_2O + X_2 \qquad (3)$$

$$2CH_4 + O_2 + 2HX \rightarrow C_2H_2 + 2H_2 + 2H_2O + X_2, \qquad (4)$$

where X represents a halide other than fluoride and $X_2$ represents a halogen molecule other than fluorine.

The halogen gas produced during the progress of reactions (1) through (4) further reacts with methane and oxygen, whereby carbon monoxide, hydrogen, ethane, ethylene, and acetylene are produced. It is believed this takes place in accordance with the following thermodynamically favorable equations:

$$CH_4 + O_2 + X_2 \rightarrow CO + H_2O + 2HX \qquad (5)$$

$$4CH_4 + O_2 + X_2 \rightarrow 2C_2H_4 + H_2 + 2H_2O + 2HX \qquad (6)$$

$$3CH_4 + O_2 + X_2 \rightarrow 1.5C_2H_4 + 2H_2O + 2HX \qquad (7)$$

$$2CH_4 + O_2 + X_2 \rightarrow C_2H_2 + 2H_2O + 2HX, \qquad (8)$$

where X represents a halide other than fluoride and $X_2$ represents a halogen molecule other than fluorine. In this fashion, the hydrogen halide catalyst is regenerated and can be recycled for re-use.

In an alternative embodiment of the present invention, a mixture of gaseous hydrogen halide (other than fluoride) and gaseous halogen (other than fluorine) can also be used as recyclable active catalysts. Furthermore, if the mole ratio of methane to oxygen exceeds about 1:1, use of a mixture of hydrogen halide and halogen as catalysts in the reactant mixture enhances the production of ethylene and acetylene. It is believed this occurs according to the following equations:

$$2CH_4 + X_2 \rightarrow C_2H_6 + 2HX \qquad (9)$$

$$2CH_4 + X_2 \rightarrow C_2H_4 + H_2 + 2HX \qquad (10)$$

$$2CH_4 + X_2 \rightarrow C_2H_2 + 2H_2 + 2HX, \qquad (11)$$

where X is a halide other than fluoride and $X_2$ is a halogen molecule other than fluorine.

Superior results are obtained when the hydrogen halide used is hydrogen bromide, the halogen used is bromine, and the reactants are present in the following molar ratios: methane to oxygen, between about 10:1 and about 1:1, methane to hydrogen bromide, between about 20:1 and about 1:1, and methane to bromine, between about 10:1 and about 1:1.

From the above equations, it will also be seen that a catalyst consisting of a gaseous halogen other than fluorine may also be employed in the process of the invention. In this alternative embodiment, the preferred halogen is bromine gas, which is present in a molar ratio of methane to bromine of between about 10:1 and about 1:1.

An important feature of my process from a practical standpoint is that exothermic or substantially thermoneutral reactions are involved. Therefore, once the reactor is brought to a specific temperature capable of sustaining pyrolytic oxidation little or no additional heat need be supplied as the reaction progresses. Furthermore, destructive flames in the reactor can easily be avoided by proper control of specific temperature for the reaction and/or by selecting the optimum operational reactant composition and temperature. In this regard, it is well known that the hydrogen halides and halogens, and in particular hydrogen bromide and bromine, are superior flame retardants. In addition, the use of air as a source of oxygen helps prevent the formation of destructive flame because it includes additional unreactive species, such as nitrogen. Finally, an important feature of the invention is that the conversion proceeds without substantial production of undesirable by-products, such as solid carbon soot.

The preferred catalyst, hydrogen bromide, is separated from the products by any means well known in the art and is recycled to the reactant mixture. In case of the use of a mixture of hydrogen halide and halogen as homogeneous catalyst, a convenient way of producing free halogen from hydrogen halide is in accordance with the following equation:

$$4HX + O_2 \rightarrow 2X_2 + 2H_2O, \qquad (12)$$

where X is a halide other than fluoride and $X_2$ is a halogen molecule other than fluorine. This reaction will proceed catalytically at relatively low temperatures. The catalysts, hydrogen halide and/or halogen, can be substantially separated from the water vapor by means well known in the art, and can then be recycled to the reactant mixture. Complete separation of water vapor from product gases is not needed, since small amounts of water vapor in the recycled catalyst can be tolerated.

In order to illustrate the invention further, the following specific examples are given.

EXAMPLE 1

Methane is reacted with oxygen in air in the presence of hydrogen bromide at a temperature of about 850° C. and atmospheric pressure. The mole ratios of the reaction mixture are as follows: methane to hydrogen bromide, about 2.5:1, and methane to oxygen in air, about 3.5:1. The reaction proceeds to yield products until between 25% and 50% of the methane is converted. The product mixture yields principally carbon monoxide, hydrogen, ethylene, acetylene, water vapor, excess unreacted methane, and small amounts of higher homologues and oxygenated derivatives. The catalyst, hydrogen bromide, remains substantially unchanged. The major products are carbon monoxide, hydrogen, and water vapor; the minor products are ethylene and acetylene. However, there are significant yields of both major and minor products.

EXAMPLE 2

The procedure of Example 1 is followed at a temperature of about 800° C., except that an additional catalyst, bromine, is added to provide the following mole ratios of reactants: methane to hydrogen bromide, about 2.5:1, methane to oxygen in air, about 4.5:1, and methane to bromine, about 3.0:1. The reaction proceeds to yield products until about 25% to 50% of the methane is converted. The principal products are similar to those in Example 1. The sum of the yields of ethylene and acetylene and the yields of carbon monoxide and hydrogen are at substantially equivalent levels.

EXAMPLE 3

The procedure of Example 1 is followed at temperature of about 800° C. except that bromine instead of hydrogen bromide is used as catalyst in the following mole ratios of reactants: methane to bromine, about 2:1, and methane to oxygen in air, about 3:1. The reaction proceeds to yield products until about 25% to 40% of the methane is converted. The principal products are the same as in Example 2, with some additional small amounts of brominated hydrocarbons. The major products are ethylene, acetylene, and hydrogen; the minor products are carbon monoxide and water vapor. However, there are significant yields of both major and minor products.

The invention has been described with particular reference to the conversion of methane into synthesis gas and higher molecular weight saturated and unsaturated hydrocarbons. However, it is to be understood that the invention is applicable to the conversion of normally gaseous hydrocarbons generally. It is also to be understood that other hydrogenated species with mobile hydrogen, such as hydrogen sulfide, can also be used as homogeneous gas phase catalysts in the process. Such species may be used as catalyst with or without the presence of a halogen gas in substantially the same quantities as described above for hydrogen halide or hydrogen halide/halogen catalytic systems. In addition, although the invention has been described with particular reference to homogeneous gas phase catalysis, it will be understood that solid metal oxide catalysts, such as silica or alumina as described in Gorin U.S. Pat. No. 2,488,083, may be used in combination with the gas phase catalysts described herein to reduce the temperatures required during pyrolytic oxidation. Use of such heterogeneous catalysts in addition to the homogeneous catalysts described herein also results in the production of significant yields of oxygenated derivatives, such as formaldehyde and methanol.

I claim:

1. A process for preparing carbon monoxide, hydrogen, and one or more saturated or unsaturated higher molecular weight hydrocarbons which comprises: reacting methane and free oxygen in the presence of gaseous hydrogen halide catalyst other than hydrogen fluoride under conditions that permit the pyrolytic oxidation of said methane and regeneration of said gaseous catalyst.

2. The process of claim 1 in which said hydrogen halide catalyst is hydrogen bromide.

3. The process of claim 1 in which said methane, oxygen, and hydrogen halide catalyst are present in the following molar ratios: methane to oxygen, between about 10:1 and about 1:1, and methane to hydrogen halide, between about 20:1 and about 1:1.

4. A process for preparing carbon monoxide, hydrogen, and one or more saturated or unsaturated higher molecular weight hydrocarbons which comprises: reacting methane and free oxygen in the presence of catalyst comprised of a mixture of a gaseous hydrogen halide other than hydrogen fluoride and gaseous halogen other than fluorine under conditions that permit the pyrolytic oxidation of said methane and regeneration of said gaseous hydrogen halide.

5. The process of claim 4 in which said hydrogen halide is hydrogen bromide and said halogen is bromine.

6. The process of claim 4 in which said methane, oxygen, hydrogen halide and halogen are present in the following molar ratios: methane to oxygen, between about 10:1 and about 1:1, methane to hydrogen halide, between about 20:1 and about 1:1, methane to halogen, between about 10:1 and about 1:1.

7. A process for converting methane into carbon monoxide, hydrogen, and one or more compounds selected from the group consisting of ethane, ethylene, and acetylene, which comprises: reacting methane, free oxygen, and catalyst which comprises a mixture of a gaseous hydrogen halide other than hydrogen fluoride and a gaseous halogen other than fluorine at a temperature above about 500° C. and below about 1000° C. using the following molar ratios of reactants: methane to oxygen, between about 10:1 and about 1:1, methane to hydrogen halide, between about 10:1 and about 1:1, and methane to halogen, between about 10:1 and about 1:1, wherein carbon monoxide, hydrogen, and one or more compounds selected from the group consisting of ethane, ethylene, and acetylene are produced and said gaseous hydrogen halide is substantially regenerated.

8. The process of claim 7 in which said hydrogen halide is hydrogen bromide and said halogen is bromine.

* * * * *